United States Patent [19]
Williams et al.

[11] Patent Number: 5,308,316
[45] Date of Patent: May 3, 1994

[54] ENCOSCOPIC KITNER

[75] Inventors: Donald B. Williams, Deerfield; Peter L. Visconti, Chicago, both of Ill.

[73] Assignee: Edward Weck Incorporated, Research Triangle Park, N.C.

[21] Appl. No.: 997,590

[22] Filed: Dec. 28, 1992

[51] Int. Cl.5 .............................. A61F 13/20
[52] U.S. Cl. ....................... 604/13; 604/11
[58] Field of Search ................ 604/11, 13–18, 604/904; 606/108

[56] References Cited

U.S. PATENT DOCUMENTS 5,158,535 10/1992 Paul et al. ........................ 604/11
5,203,767 4/1993 Cloyd ............................... 604/11

OTHER PUBLICATIONS

1991 O. R. Concepts, Inc. advertisement for Endoscopic Kittner-Blunt Dissecting Instrument.
1992 MedChem Products, Inc. advertisement for a Microfibrillar Collagen Hemostat in an Endoscopic Delivery System.
1992 O. R. Concepts, Inc., advertisement for among other products, an Endoscopic Kittner.

*Primary Examiner*—Randall L. Green
*Assistant Examiner*—P. Zuttarelli
*Attorney, Agent, or Firm*—Rosenblatt & Associates, P.C.

[57] ABSTRACT

An endoscopic kitner features a delivery tube with a continuous supply of absorbent material. The absorbent material is retractable into a housing as new absorbent material is placed in position for use. The spent absorbing material is movable into a housing for removal of the kitner. A hand-held drive mechanism is employed to advance the absorbent material.

10 Claims, 2 Drawing Sheets

ENCOSCOPIC KITNER

FIELD OF THE INVENTION

The field of this invention relates to endoscopic kitners.

BACKGROUND OF THE INVENTION

In the past, endoscopic procedures have required dissection and manipulation. Typically, kitners employed in the past have used an absorbing material fixedly mounted at its distal end to assist in such procedures. However, in applications that require an extensive amount of absorbency to deal with the particular situation, the absorbent capacity of the material at the distal end of the kitner is quickly consumed. In prior designs, this has required removal of the kitner, which is generally inserted through a 10-mm trocar sheath. The process of removal and reinsertion with a new absorbent material attached to the distal tip is cumbersome and time-consuming. Additionally, in past designs, the absorbent material is exposed to other sites as it is being withdrawn from the region where the procedure is occurring.

It is the object of this invention to present an endoscopic kitner that allows replenishment of the extended kitner material at the distal tip to allow the procedure to continue without necessitating the removal of the kitner for renewal of the absorbent material. It is a further object of this invention to reposition the spent absorbent material in such a manner so as to shield it from exposure to other parts of the body away from the procedure site as the kitner is being removed. In accordance with the objects of the invention, a kitner has been developed that allows progressive feeding of kitner material while the distal tip of the kitner is at the procedure site. Additionally, through the continuous feeding mechanism, the spent kitner material is retractable into a housing to prevent contact between any other parts of the body and the spent kitner material as the kitner is being removed from the procedure site.

SUMMARY OF THE INVENTION

An endoscopic kitner features a delivery tube with a continuous supply of absorbent material. The absorbent material is retractable into a housing as new absorbent material is placed in position for use. The spent absorbing material is movable into a housing for removal of the kitner. A hand-held drive mechanism is employed to advance the absorbent material.

DETAILED DESCRIPTION OF THE PREFERRED EMBODIMENT

Figure 1:
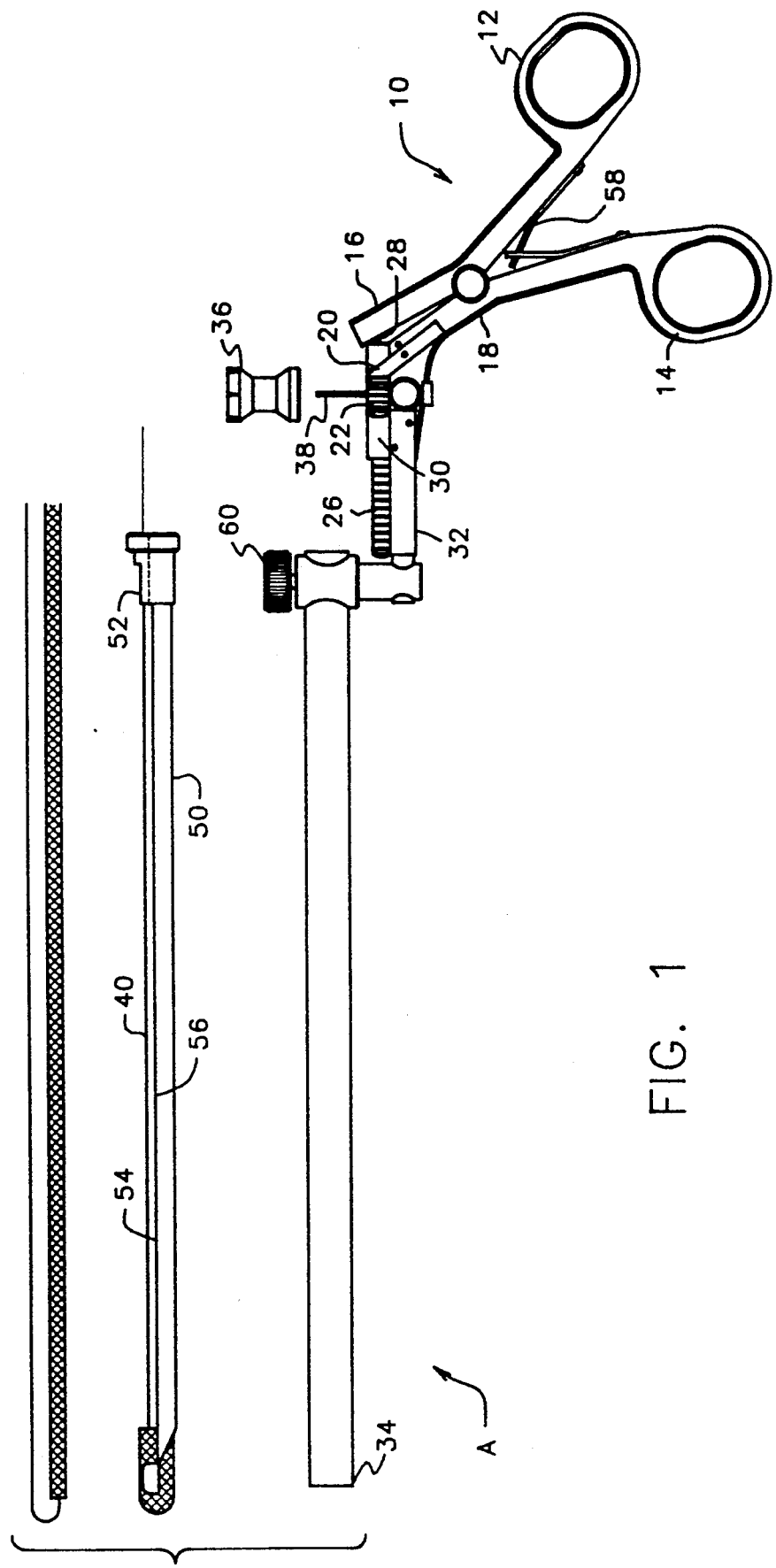
FIG. 1 represents an exploded view, showing the components of the preferred embodiment of the endoscopic kitner.

The apparatus A is illustrated in FIG. 1. The apparatus A has a handle mechanism 10, which features finger grips 12 and 14. Finger grips 12 and 14 are connected to levers 16 and 18. A dog 20 is mounted to lever 18. Dog 20 selectively engages pinion 22 and acts as a ratchet, permitting rotation in one direction and precluding rotation in the opposite direction. The direction of rotation of pinion 22 is indicated by arrow 24 of FIG. 2. By virtue of the operation of finger grips 12 and 14, bringing them closer together, lever 16 moves away from lever 18. Lever 16 is connected to rack 26 through connecting rod 28. A guide tube 30 is mounted to handle 18, more specifically to extension 32, which is connected to handle 18.

The action of moving finger grips 12 and 14 closer together pulls lever 16 away from end 34. As a result, rod 28 pulls on rack 26. This allows pinion 22 to rotate in the direction shown by arrow 24. Rotation of pinion 22 causes spool 36, which is mounted to spindle 38, to rotate in the direction of arrow 24.

Figure 2:
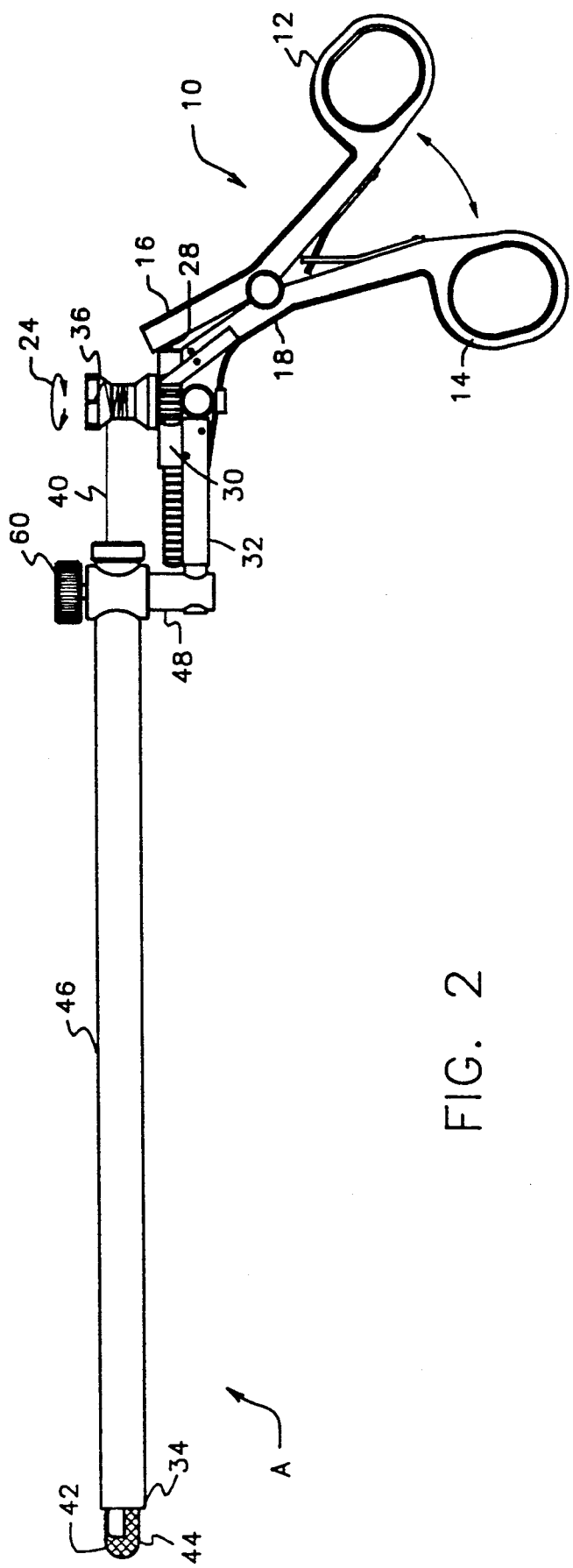
FIG. 2 is an assembly drawing of the endoscopic kitner shown in FIG. 1.

As seen in FIG. 2, rotation of spool 36 results in string 40 winding around spool 36. The winding action of string 40 around spool 36 advances the kitner material 42 in the direction of arrow 44. As shown in FIG. 2, a portion of kitner material 42 extends beyond end 34 of tube 46. Tube 46, in the preferred embodiment, is secured to a pillar 48, which is mounted to extension 32. As shown in FIG. 1, an insert 50 is adapted to be inserted into tube 46. Insert 50 has a flat 52, which helps to secure the proper orientation of insert 50 into tube 46. A mating surface inside tube 46 (not shown) cooperates with flat 52 to ensure the proper orientation. Insert 50 has an upper path 54 and a lower path 56 for the kitner material 42. Initially, the kitner material 42 is disposed entirely along the lower path 56, as illustrated in FIG. 1., top view. Several repetitions of movement of finger grips 12 and 14 advance the kitner through the rack and pinion action of rack 26 and pinion 22 to the position shown in the middle view of FIG. 1. At this point, the apparatus A is ready for use internally. The kitner material 42 can be advanced to the position shown in the middle view of FIG. 1 as the apparatus A is inserted into the trocar (not shown) or after the apparatus A is at the procedure site.

Those skilled in the art will appreciate that once the apparatus A is at the procedure site, repetitive operation of finger grips 12 and 14 advances the kitner material 42 from lower path 56 to upper path 54. The segments of the kitner material 42 which are exposed beyond end 34 can be changed with actuation of finger grips 12 and 14. Therefore, during the procedure, the kitner material 42 can be advanced so that the consumed kitner material 42 is retracted back into tube 46 and along upper path 54.

The tube 46 can be made of any variety of materials, including stainless steel or suitably rigid plastics. The handle portion including levers 16 and 18 can be reused with different inserts 50 and kitner material 42 mounted to such inserts 50. Different mechanical or pneumatic means can be employed to advance the continuous kitner material 42 without departing from the spirit of the invention. Similarly, different materials can be used for string 40, such as cotton or plastic, without departing from the spirit of the invention. It is also within the scope of the invention to directly connect a continuous kitner material 42 to a driving mechanism for its advancement without the use of any intermediate linkages such as a string 40.

Those skilled in the art will appreciate that the tension in string 40 is maintained by virtue of the interaction between dog 20 and pinion 22. Springs 58 return the finger grips 12 and 14 to their neutral position shown in FIG. 1. Knob 60 is used to releasably secure the tube 46 to the pillar 48. The apparatus A can be used continuously until the kitner material 42 is fully advanced onto upper path 54. The direction of movement of the kitner material 42 can be reversed without departing from the spirit of the invention.

The foregoing disclosure and description of the invention are illustrative and explanatory thereof, and various changes in the size, shape and materials, as well as in the details of the illustrated construction, may be made without departing from the spirit of the invention.

We claim:

1. An instrument for surgical procedures that feeds and retracts absorbent material, comprising:
   an elongated housing;
   gripping means on said housing for manipulation of said housing;
   absorbent material movably mounted to said housing;
   means for feeding said absorbent material so that at least a portion thereof selectively extends beyond said housing to replace a portion of said absorbent material which has been retracted into said housing.

2. The instrument of claim 1, wherein:
   said means for feeding moves said absorbent material with respect to said housing.

3. The instrument of claim 2, wherein:
   said means for feeding moves a portion of said absorbent material in one direction in said housing, while another portion of said absorbent material is moved in an opposite direction in said housing.

4. The instrument of claim 3, wherein:
   said means for feeding first feeds said absorbent material beyond said housing and, upon further actuation, retracts a portion previously extending beyond said housing back into said housing.

5. The instrument of claim 4, wherein said means for feeding further comprises:
   a linkage;
   said gripping means connected to said linkage for selective advancement of said absorbent material.

6. The instrument of claim 5, wherein:
   said linkage comprises an elongated flexible strand, said means for feeding further comprises a take-up spool;
   whereupon actuation of said gripping means said strand is wrapped on said spool to advance said absorbent material.

7. The instrument of claim 6, wherein means for feeding further comprises:
   a rack and pinion assembly actuated by said gripping means;
   said spool is mounted to a spindle connected to said assembly;
   whereupon actuation of said gripping means, said spindle is driven by said assembly, taking up said strand on said spool to advance said absorbent material.

8. The instrument of claim 7, further comprising:
   a ratchet selectively engageable to said assembly to limit rotation of said spindle to one direction to retain tension on said strand.

9. The instrument of claim 8, further comprising:
   an insert member adapted for removable mounting to said housing;
   said insert member supporting said absorbent material and replaceable as a unit with said absorbent material.

10. The instrument of claim 1, further comprising:
    an insert member adapted for removable mounting to said housing;
    said insert member supporting said absorbent material and replaceable as a unit with said absorbent material.

* * * * *